(12) United States Patent
Horn et al.

(10) Patent No.: US 11,109,938 B2
(45) Date of Patent: Sep. 7, 2021

(54) MULTI-SPOT LASER PROBE WITH ILLUMINATION FEATURES

(71) Applicant: Novartis AG, Basel (CH)

(72) Inventors: Jochen Horn, Pleasanton, CA (US); Alireza Mirsepassi, Irvine, CA (US); Chenguang Diao, Irvine, CA (US); Mark Harrison Farley, Laguna Hills, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 134 days.

(21) Appl. No.: 16/175,962

(22) Filed: Oct. 31, 2018

(65) Prior Publication Data

US 2019/0142544 A1 May 16, 2019

Related U.S. Application Data

(60) Provisional application No. 62/585,631, filed on Nov. 14, 2017.

(51) Int. Cl.
| | |
|---|---|
| *A61F 9/008* | (2006.01) |
| *A61B 90/30* | (2016.01) |
| *F21V 8/00* | (2006.01) |
| *A61B 18/20* | (2006.01) |
| *A61B 18/22* | (2006.01) |

(52) U.S. Cl.
CPC .............. *A61B 90/30* (2016.02); *A61F 9/008* (2013.01); *A61F 9/00821* (2013.01); *A61F 9/00823* (2013.01); *G02B 6/0006* (2013.01); *G02B 6/0008* (2013.01); *A61B 2018/208* (2013.01);
(Continued)

(58) Field of Classification Search
CPC .............. A61B 90/30; A61B 2018/208; A61B 2090/306; A61B 2018/2211; A61F 9/008; A61F 9/00823; A61F 9/00821; A61F 2009/00863; G02B 6/0006; G02B 6/0008
See application file for complete search history.

(56) References Cited

U.S. PATENT DOCUMENTS

| | | | |
|---|---|---|---|
| 5,201,730 | A | 4/1993 | Easley |
| 5,275,593 | A | 1/1994 | Easley et al. |

(Continued)

FOREIGN PATENT DOCUMENTS

| | | |
|---|---|---|
| KR | 20140009317 A | 1/2014 |
| WO | 2008024848 A2 | 2/2008 |

(Continued)

*Primary Examiner* — Rex R Holmes

(57) ABSTRACT

Multi-fiber laser probes utilize relative motion of fibers and other laser probe elements to preserve small-gauge compatibility while providing for multi-spot beam deliver, or to provide for the selectively delivery of single-spot or multi-spot beam patterns. An example probe includes fibers having distal ends that are movable as a group onto a distal ramp element affixed to a distal end of a cannula, so that the distal ends of the fibers can be moved between a retracted position, in which the distal ends of the fibers are within the cannula or ramp element, and an extended position, in which distal ends of the fibers are guided by grooves or channels of the ramp so as to extend at least partially through external openings in the distal end of the laser probe and so as to be pointed angularly away from a longitudinal axis of the cannula.

8 Claims, 13 Drawing Sheets

(52) U.S. Cl.
CPC . *A61B 2018/2211* (2013.01); *A61B 2090/306* (2016.02); *A61F 2009/00863* (2013.01)

(56) References Cited

U.S. PATENT DOCUMENTS

| | | | |
|---|---|---|---|
| 5,591,160 A | 1/1997 | Reynard | |
| 5,651,783 A | 7/1997 | Raynard | |
| 7,566,173 B2 | 7/2009 | Auld et al. | |
| 7,783,346 B2 | 8/2010 | Smith et al. | |
| 8,561,280 B2 | 10/2013 | Diao et al. | |
| 8,571,364 B2 | 10/2013 | Smith et al. | |
| 8,764,261 B2 | 7/2014 | Smith | |
| 8,939,964 B2 | 1/2015 | Smith | |
| 8,951,244 B2 | 2/2015 | Smith | |
| 8,968,347 B2 | 3/2015 | McCollam | |
| 9,055,885 B2 | 6/2015 | Horvath | |
| 9,089,364 B2 | 7/2015 | Bhadri | |
| 9,364,982 B2 | 6/2016 | Schaller | |
| 9,402,643 B2 | 8/2016 | Auld | |
| 9,561,085 B2 | 2/2017 | Yadlowsky | |
| 9,839,749 B2 | 12/2017 | Johnson | |
| 9,956,053 B2 | 5/2018 | Diao | |
| 10,016,248 B2 | 7/2018 | Mirsepassi | |
| 10,039,669 B2 | 8/2018 | Heeren | |
| 10,245,181 B2 | 4/2019 | Diao | |
| 10,278,785 B2 | 5/2019 | Mirsepassi | |
| 10,295,718 B2 | 5/2019 | Mirsepassi | |
| 2007/0265602 A1* | 11/2007 | Mordaunt | A61F 9/00821 606/4 |
| 2008/0051770 A1 | 2/2008 | Scheller et al. | |
| 2009/0161384 A1 | 6/2009 | Smith | |
| 2009/0182313 A1 | 7/2009 | Auld | |
| 2011/0144627 A1 | 6/2011 | Smith | |
| 2012/0191078 A1 | 7/2012 | Yadlowsky et al. | |
| 2013/0079598 A1 | 3/2013 | Auld et al. | |
| 2013/0150839 A1 | 6/2013 | Smith et al. | |
| 2014/0121469 A1 | 5/2014 | Meckel | |
| 2014/0180264 A1* | 6/2014 | Diao | A61F 9/00821 606/4 |
| 2014/0194862 A1 | 7/2014 | Smith et al. | |
| 2014/0200566 A1 | 7/2014 | Smith | |
| 2014/0250668 A1 | 9/2014 | Smith | |
| 2014/0293225 A1* | 10/2014 | Parto | A61F 9/00821 351/208 |
| 2015/0219819 A1* | 8/2015 | Sun | C03C 25/10 362/553 |
| 2016/0174812 A1 | 6/2016 | Artsyukhovich | |
| 2017/0014023 A1 | 1/2017 | Kern | |
| 2017/0014267 A1 | 1/2017 | Kern | |
| 2017/0119491 A1 | 5/2017 | Mirsepassi | |
| 2017/0165114 A1 | 6/2017 | Hallen | |
| 2017/0172792 A1 | 6/2017 | Mirsepassi | |
| 2017/0176660 A1* | 6/2017 | Mirsepassi | A61F 9/00736 |
| 2018/0055596 A1 | 3/2018 | Johnson | |
| 2018/0132963 A1 | 5/2018 | Diao | |
| 2018/0133057 A1 | 5/2018 | Diao | |
| 2018/0168768 A1 | 6/2018 | Mirsepassi | |
| 2018/0168861 A1 | 6/2018 | Mirsepassi | |
| 2018/0243136 A1 | 8/2018 | Diao | |
| 2018/0243137 A1* | 8/2018 | Diao | A61B 18/22 |
| 2018/0333304 A1 | 11/2018 | Diao | |
| 2018/0338776 A1 | 11/2018 | Farley | |
| 2018/0338859 A1 | 11/2018 | Mirsepassi | |
| 2018/0338860 A1 | 11/2018 | Farley | |
| 2018/0344528 A1 | 12/2018 | Farley | |
| 2019/0175405 A1 | 6/2019 | Diao | |

FOREIGN PATENT DOCUMENTS

| | | |
|---|---|---|
| WO | 2008024848 A3 | 6/2008 |
| WO | 2018220488 A1 | 12/2018 |
| WO | WO2018220488 A1 | 12/2018 |

* cited by examiner

MULTI-SPOT LASER PROBE WITH ILLUMINATION FEATURES

PRIORITY CLAIM

This application claims the benefit of priority of U.S. Provisional Patent Application Serial No. 62/585,631 titled "MULTI-SPOT LASER PROBE WITH ILLUMINATION FEATURES," filed on Nov. 14, 2017, whose inventors are Jochen Horn, Alireza Mirsepassi, Chenguang Diao, Mark Harrison Farley and Ronald T. Smith, which is hereby incorporated by reference in its entirety as though fully and completely set forth herein.

TECHNICAL FIELD

This application relates to laser probes for use in ophthalmic procedures and more particularly to multi-spot laser probes having illumination features.

BACKGROUND

Laser photocoagulation therapy addresses ocular conditions such as retinal detachments and tears as well as proliferative retinopathy resulting from diseases such as diabetes. The abnormally high blood sugar in a diabetic stimulates the retinal vessels to release growth factors that in turn encourage an undesirable proliferation of blood vessels and capillaries over the retinal surface. These proliferated blood vessels are very delicate and will readily bleed into the vitreous. The body responds to the damaged vessels by producing scar tissue, which may then cause the retina to detach so as to eventually cause blindness.

In laser photocoagulation, a laser probe is used to cauterize the blood vessels at various laser burn spots across the retina. Because the laser will also damage the rods and cones that are present in the retina to allow vision, eyesight, as well as the blood vessels, is affected. Since vision is most acute at the central macula of the retina, the surgeon arranges the resulting laser burn spots in the peripheral areas of the retina. In this fashion, some peripheral vision is sacrificed to preserve central vision. During the procedure, the surgeon drives the probe with a non-burning aiming beam such that the retinal area to be photocoagulated is illuminated. Due to the availability of low-power red laser diodes, the aiming beam is generally a low-power red laser light. Once the surgeon has positioned the laser probe so as to illuminate a desired retinal spot, the surgeon activates the laser through a foot pedal or other means to then photocoagulate the illuminated area. Having burned a retinal spot, the surgeon repositions the probe to illuminate a new spot with the aiming light, activates the laser, repositions the probe, and so on until a suitable array of burned laser spots are distributed across the retina.

The number of required laser photocoagulations for any one treatment of the retina is large. For example, 1,000 to 1,500 spots are commonly burned. It may thus be readily appreciated that if the laser probe was a multi-spot probe enabling the burning of multiple spots at a time, the photocoagulation procedure would be faster (assuming the laser source power is sufficient). Accordingly, various multi-spot laser probes have been developed, with these probes being classifiable into two categories. A first category, denoted herein as a "multi-fiber, multi-spot" laser probe, produces its multiple laser beams through a corresponding array of optical fibers. A second category uses only a single fiber and is thus denoted herein as a "single-fiber, multi-spot" laser probe.

During an ophthalmic procedure, such as endolaser photocoagulation, the surgeon may need to perform self-sclera depression, or bimanual surgery. They may also need additional task lighting on the probe. Illuminated laser probes provide a solution for these cases, but the current design of fiber optics impose limitations on the probe, because of the materials and the sizes involved. For instance, currently available plastic optical fiber is typically more than 100 microns in diameter, and occupies a substantial portion of the probe's cannula, leaving little room for other components. The efficiency of these fibers for carrying visible light is low, which means that the resulting brightness of the illumination may be very low. Further, plastic fiber is prone to thermal damage.

Accordingly, there is a need in the art for multi-spot laser probes with improved illumination features.

SUMMARY

The need for improved illumination features in a multi-spot laser probe is addressed by several embodiments disclosed herein and illustrated in the attached figures. An example multi-fiber, multi-spot laser probe according to some of these embodiments includes a plurality of fibers extending from a proximal end of the laser probe to at least near a distal end of the laser probe, where the proximal end of the laser probe is configured to be coupled to a laser source via an adapter interface. This example probe further includes a cannula having a distal end and surrounding the plurality of fibers along at least a portion of the laser probe at or near the distal end of the laser probe, as well as an illumination fiber extending from the proximal end of the laser probe to at least near the distal end of the laser probe. This illumination fiber has a diameter substantially smaller than corresponding diameters for the plurality of fibers and is arranged, at the proximal end of the fiber, for coupling to a visible light source via the adapter interface.

The illumination fiber in some of these embodiments may have a diameter of less than 50 microns, compared to, for example, a diameter of at least 90 microns for the other fibers. In some embodiments, the illumination fiber extends along the laser probe within the cannula, e.g., at or near the longitudinal center of the cannula. In other embodiments, the illumination fiber extends along the laser probe outside the cannula, along an exterior surface of the cannula.

Other embodiments of a laser probe as disclosed herein include one or more fibers extending from a proximal end of the laser probe to at least near a distal end of the laser probe, where the proximal end of the laser probe is configured to be coupled to a laser source via an adapter interface, as well as a cannula having a distal end and surrounding the one or more fibers along at least a portion of the laser probe at or near the distal end of the laser probe. In these embodiments, a light-emitting diode is attached to the cannula at or near the distal end of the cannula, the light-emitting diode being electrically coupled to a power source via the adapter interface. In some embodiments, this light-emitting diode forms part of a light-emitting diode ring that encircles the cannula at or near the distal end of the cannula.

DETAILED DESCRIPTION

As discussed above, improvements in illumination features are need for multi-spot laser probes. Embodiments reflecting multiple approaches to addressing this problem are disclosed herein, and may be categorized into three groups:

probes utilizing a nanofiber for illumination delivery;
probes using the same fiber to carry the multi-spot laser light and an illumination beam; and
probes using LED-based illumination.

Several of the disclosed embodiments are compatible with multi-fiber, multi-spot laser probes, while others are compatible with single-fiber, multi-spot laser probes. While several of the embodiments described in detail herein are explained and illustrated in the context of particular multi-fiber, multi-spot probes, it will be appreciated that these embodiments may be readily adapted to single-fiber, multi-spot probes. Likewise, it will be appreciated that those embodiments described herein in the context of a single-fiber, multi-spot probe may be adapted to a multi-fiber, multi-spot probe.

Figure 1:
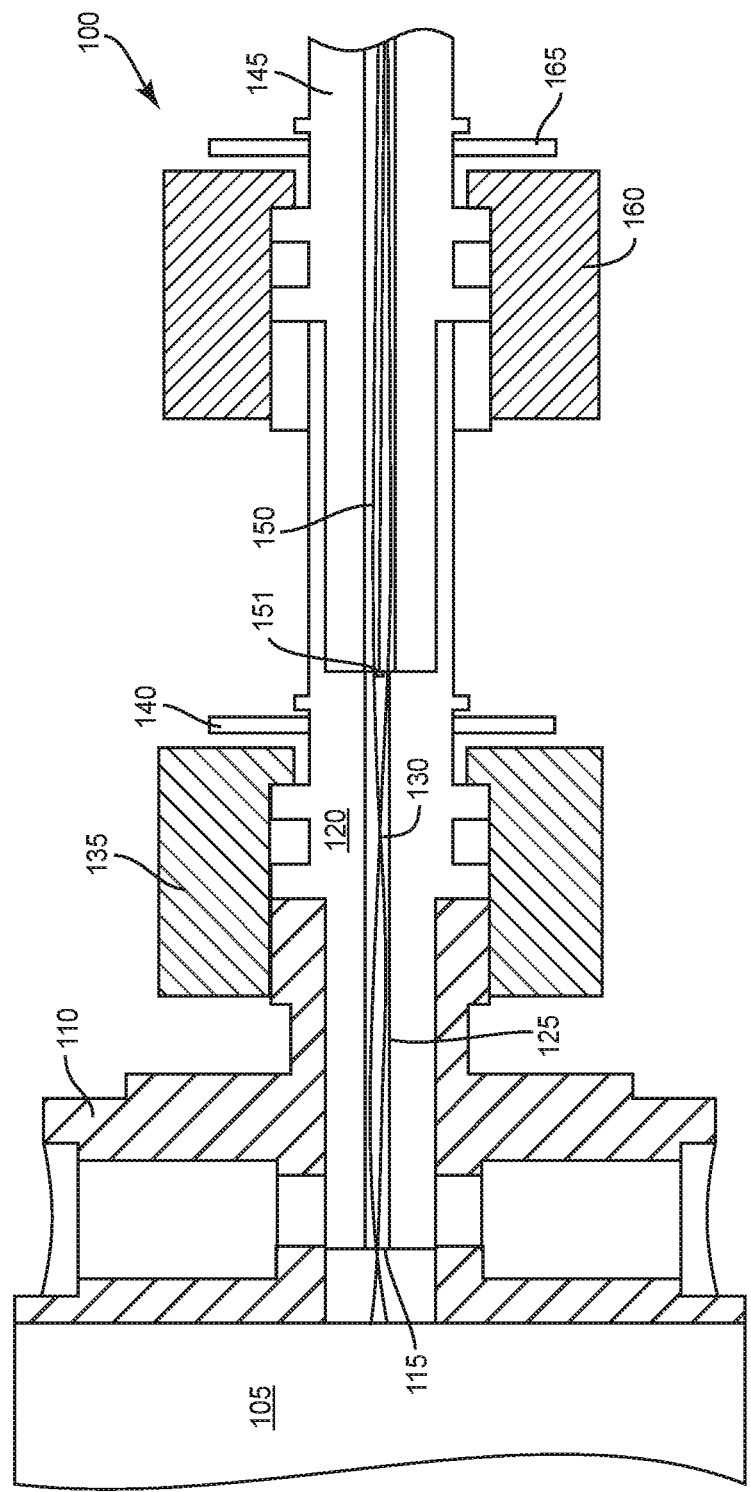
FIG. 1 is a longitudinal cross-sectional view of a laser source coupled to an adapter element containing a gradient-index (GRIN) lens for coupling to a proximal end of a multi-fiber, multi-spot laser probe.

Turning now to the drawings, certain details of a multi-fiber, multi-spot laser probe 100 are shown in FIG. 1. Not shown in FIG. 1 are details of the proximal end of laser probe 100; details of several realizations of the proximal end are provided below. The portions of the multi-fiber, multi-spot laser probe 100 shown in FIG. 1 are also illustrated in U.S. Pat. No. 8,951,244; thus, it will be appreciated that the details shown in FIG. 1 represent an example of the prior art. It should be noted that the illumination-related techniques and devices discussed further below are compatible with the laser probe 100, but may also be compatible with laser probes having differing designs at the proximal end.

Returning to FIG. 1, it can be seen that a laser source 105 drives probe 100 through a suitable interconnect. A common standardized interconnect for laser source 105 is a subminiature version A (SMA) adapter. Thus, laser source 105 includes a female SMA adapter 110. However, it will be appreciated that laser probe 100 is readily adapted to mate with any conventional standardized optical interconnect so long as the laser source's interconnect presents a focused beam spot such as laser waist 115 to a proximal end of a male connector from the laser probe. Thus, the following discussion will assume that laser probe 100 couples to source 105 through a customized SMA adapter 120 without loss of generality.

To receive laser waist 115, the bore of SMA adapter 120 includes a gradient index (GRIN) lens 125. GRIN lens 125 may be a simple, single-element cylindrical GRIN rod lens that is readily inserted into such a bore. GRIN lens 125 is designed to relay the focused beam to a second focused spot 130 and then to a collimated beam wave front at its distal end. As known in the SMA arts, SMA adapter 120 secures to SMA adapter 110 through a threaded cylinder 135 and retaining ring 140. SMA adapter 120 has both a male end for insertion into SMA adapter 110 but also a female end that receives a conventional optical interconnect such a male SMA 905 fiber connector 145. Connecter 145 secures to adapter 120 through a threaded cylinder or ring 160 and retaining ring 165. Connector 145 includes in its bore an array of optical fibers 150. A proximal end 151 of array 150 is separated from the distal end of GRIN lens 125 by a suitable air gap such as a 220 µm air gap. Connector 145 connects to a flexible cable encasing fibers 150 that leads to a handpiece and cannula, as known in the laser probe arts.

Figure 2:
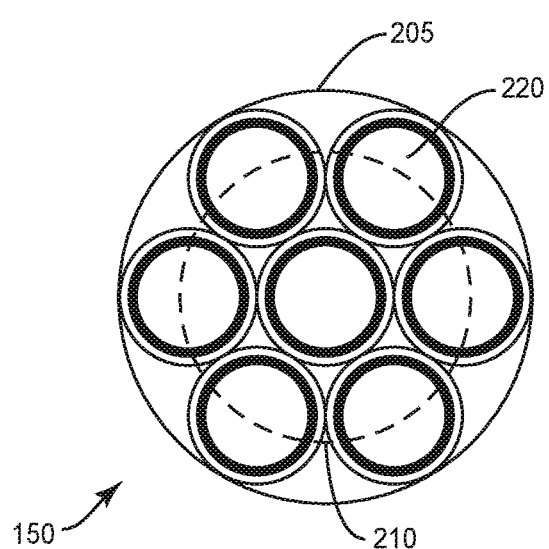
FIG. 2 shows a radial cross-sectional view of a multi-fiber array within the proximal end of the probe of FIG. 1.

An example embodiment of fiber array 150 is shown in cross-section in FIG. 2. The laser beam boundary at the proximal end 151 of FIG. 1 is shown for both a green laser beam boundary 205 from source 105 as well as a red aiming beam boundary 210. Array 150 includes a central fiber circumferentially surrounded by six outer fibers. In one embodiment, each fiber 220 has a numerical aperture (NA) of 0.22 achieved through a 75 µm glass core encased in a 90 µm cladding, surrounded by a 101 µm jacket. To minimize the amount of uncoupled laser energy into array 150, GRIN lens 125 is configured such that laser beam boundary 205 just encompasses the six outer fibers. The clocking of array 150 relative to the laser beam is not an issue as the laser beam and array 150 are at least generally axisymmetric. Array 150 extends to a distal end of the laser probe; details of several embodiments of the distal end of the laser probe are discussed in more detail below.

The advantageous properties of such a proximal interconnection in that no complicated, multi-lens relay system is required. Instead, GRIN lens 125 is readily inserted into the bore of adapter 120 that enables a standardized adapter such as male SMA adapter 145 to attach a disposable laser probe receiving fiber array 150. Without GRIN lens 125 and its adapter 120, standardized adapter 110 on laser source 105 would have to be changed, which is plainly undesirable since other attachments for source 105 would have to change in concert. Alternatively, the source's adapter could be left standardized but then a multi-lens relay system would be required. However, SMA adapter 120 and GRIN lens 125 eliminate such complications. Although SMA adapter 120 is thus quite advantageous, one can appreciate that roughly 50% of the laser energy is delivered to the interstices between the fibers in array 150 as seen in FIG. 2. This laser energy is thus unavailable for use in photocoagulation, thereby increasing the necessary laser source power and/or the amount of time necessary to produce the laser burn spots.

Figure 3:
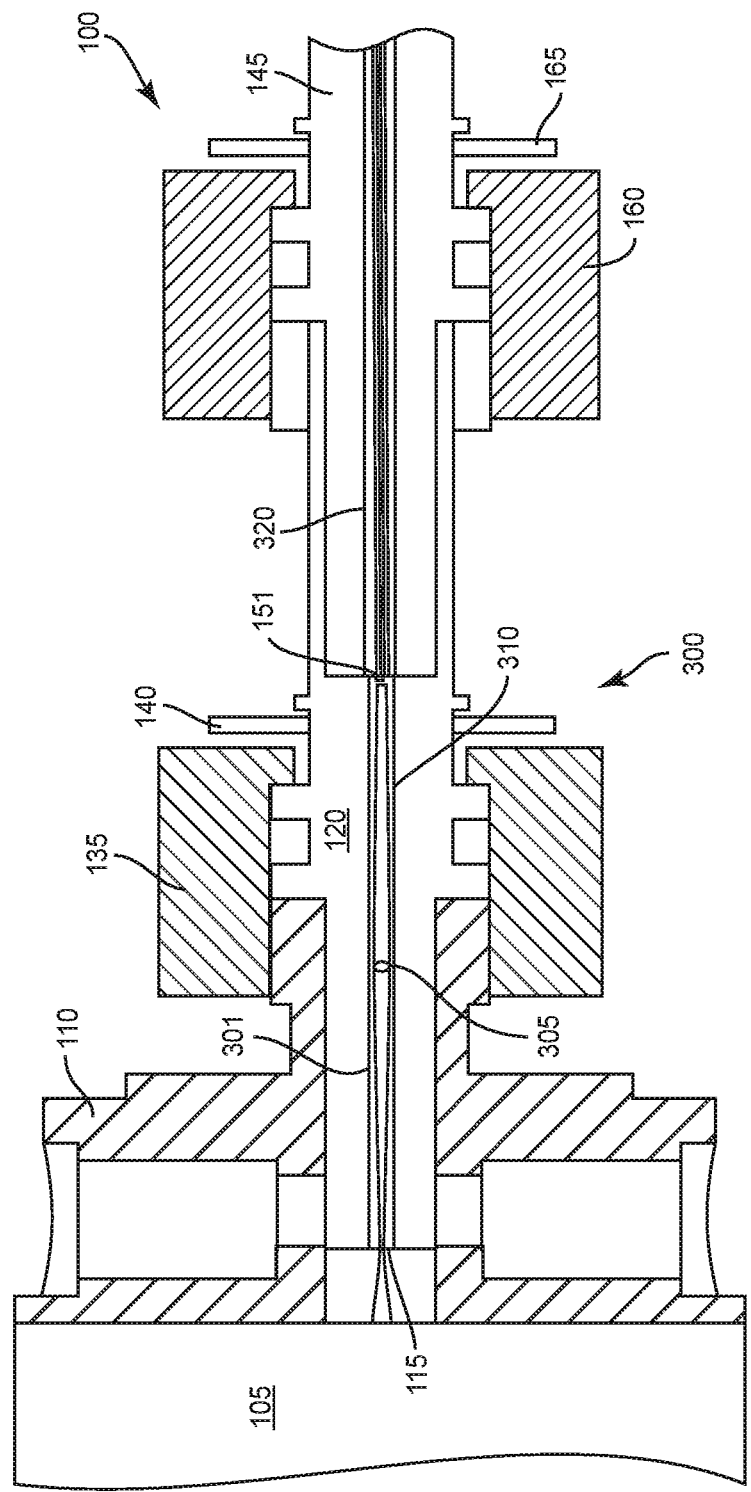
FIG. 3 is a longitudinal cross-sectional view of a laser source coupled to an adapter element including two gradient-index (GRIN) lenses and a diffractive beam splitter for coupling to a proximal end of a multi-fiber, multi-spot laser probe.
Figure 4:
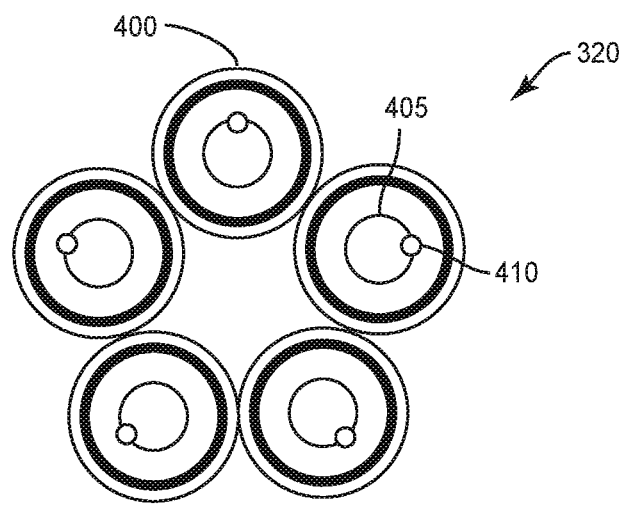
FIG. 4 is a radial cross-sectional view of a multi-fiber array within the proximal end of the probe of FIG. 3.

Turning now to FIG. 3, a diffractive embodiment that does not illuminate fiber array interstices is illustrated. As discussed with regard to FIG. 1, customized SMA adapter 120 permits a user to conveniently attach a disposable probe to adapter 120 to drive laser energy onto a fiber array. In the embodiment shown in FIG. 3, however, adapter 120 includes in its bore a diffractive beam splitter 305 arranged between a first GRIN lens 301 and a second GRIN lens 310. GRIN lens 301 is configured to collimate the laser beam diverging from laser waist 115 into a collimated wave front presented to diffractive beam splitter 305. GRIN lens 310 is configured to focus the resulting diffracted multiple laser beams from splitter 305 onto a proximal face 151 of a fiber array 320 contained within the bore of male SMA adapter 145. Fiber array 320 includes a plurality of fibers arranged according to the diffractive properties of diffractive beam splitter 305. For example, if diffractive beam splitter produces a symmetric pentagonal distribution of five diffracted beams, fiber array 320 is arranged in a corresponding pentagonal distribution. FIG. 4 shows such an arrangement for fiber bundle 320 at its proximal face 151.

In one embodiment, each optical fiber 400 has a 75 µm glass core clad in a 90 µm cladding, which in turn is surrounded by a 101 µm jacket, to achieve an NA of 0.22. The resulting projection of the diffracted green laser beams from splitter 305 is indicated by a boundary 405. Because diffraction is wavelength dependent, the projection of the aiming beam will have a different alignment with fiber array 320. Thus, splitter 305 and fiber array 320 are arranged such that boundary 405 is axially aligned with each fiber 400, whereas a boundary 410 of a red aiming beam is radially displaced with regard to a center or longitudinal axis of each fiber.

In one embodiment, the off-axis displacement provided by splitter 305 to each green diffracted beam is 1.45 degrees. GRIN lens 310 focuses the resulting collimated and diffracted beams onto the entrance face of each fiber 400 in array 320. By such an appropriate clocking of array 320 relative to the diffracted beams, efficient coupling of the respective diffracted beam and the aiming beam into each fiber 400 is achieved. In that regard, other types of adapters such as a ferrule connector (FC) or a standard connector (SC) commonly used in the telecommunications industry may be used instead of SMA adapter 120 to assist in optimal clocking. As discussed with regard to FIG. 1, assembly of the optical components into SMA adapter 120 is advantageously convenient in that GRIN lenses 301 and 310 as well as intervening diffractive beam splitter 305 may have optical adhesive applied and then slid into the bore of adapter 120 and abutted end-to-end with each other. In contrast, an alignment of refractive lenses would be cumbersome and difficult in comparison.

Figure 5:
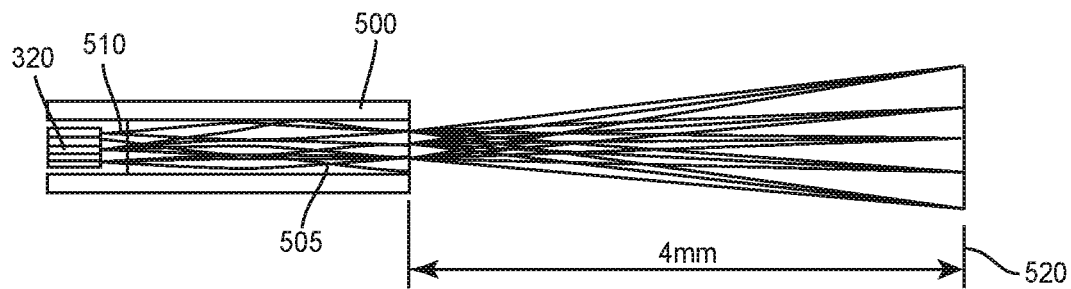
FIG. 5 illustrates a GRIN lens for angularly separating the projected multiple beams emitted from the multi-fiber array of FIG. 4.

With the laser beam from the source split and telecentrically propagated through the fiber array as discussed above with regard to either FIG. 1 or FIG. 3, there remains the issue of angularly projecting focused laser spots from the laser probe. U.S. Pat. No. 8,951,244 disclosed a GRIN lens solution, an example of which is shown in FIG. 5. It will be appreciated that while the example embodiment shown in FIG. 5 is particularly adapted for compatibility with the fiber array 320 of FIG. 3, it will be appreciated that an analogous embodiment can be readily constructed for fiber array 150 of FIG. 1.

As seen in FIG. 5, a laser probe cannula 500, e.g., a stainless-steel cannula, receives a GRIN lens 505 at its distal end. A distal end of fiber array 320 is displaced within the cannula so as to project diverging beams 510 at a proximal end face of GRIN lens 505. GRIN lens 505 then focuses the beams on the retinal surface 520. The distribution of the resulting focused beams on the retina depends on the distribution of the fibers at the distal end of array 320.

In that regard, whereas the distribution at the proximal end of array 320 (FIG. 3) should be axially symmetric, one can arrange the fibers in any suitable distribution at the distal end. For example, as seen in FIG. 5, array 320 is linearly arranged at the distal end. The resulting laser spots are thus an enlarged version of the image (in this embodiment, a linear array) presented to GRIN lens 505. In one embodiment, GRIN lens 505 focuses the angularly-distributed beams at a distance of 4 mm from the distal end of cannula 500. Advantageously, GRIN lens 505 obviates any need for: bending the fibers into the desired angular distribution (and the associated problems of such bending), beveling the distal end faces of the fibers, or adding optical elements to the distal end faces. The fibers can even be touching one another in array 320 and GRIN lens 505 will still be effective.

Many alternatives to the configuration shown in FIG. 5 for the distal end of a multi-fiber laser probe are possible, including embodiments in which the GRIN lens 505 is removed from the laser beam path at the probe's distal end, and embodiments that have no optical elements distal to the optical fibers. Some embodiments may provide actuation means to induce angular beam separation, via fiber curvature. Various embodiments provide advantages such as small-gauge compatibility and/or switchable quasi-single-spot and multi-spot beam delivery.

Some of these embodiments are detailed below, and are presented with respect to 4-fiber or 5-fiber embodiments of the invention, which are shown in axial and transverse cross section views. It will be understood, however, that the number of fibers is not limited to 4 or 5—fewer or more fibers may be used, in various embodiments. Further, the embodiments are not presented in any particular order. The embodiments disclosed herein may be implemented in laser probes that are compatible with either of the adapters described above, i.e., in FIGS. 1 and 3, which provide means for splitting the beam and focusing the resulting multiple beams into the proximal ends of optical fibers, such each fiber carries its own beam. It will be understood, however, that the embodiments described below may be implemented in laser probes having different mating configurations at the proximal end, and/or in conjunction with different adapters or interfaces for coupling a laser source or sources to the multiple fibers of the multi-fiber laser probe.

Figure 6A:
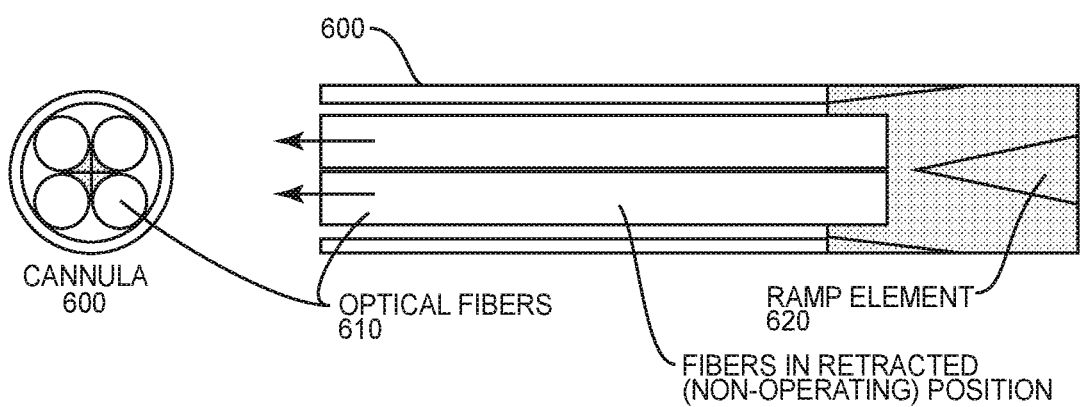
FIG. 6A and FIG. 6B illustrate an example embodiment of a distal end of a multi-fiber multi-spot laser probe that incorporates a spreading spacer at the distal end of the laser probe, configured so that fibers in the probe can be slid from a retracted, non-operating position to an extended operating position.
Figure 6B:
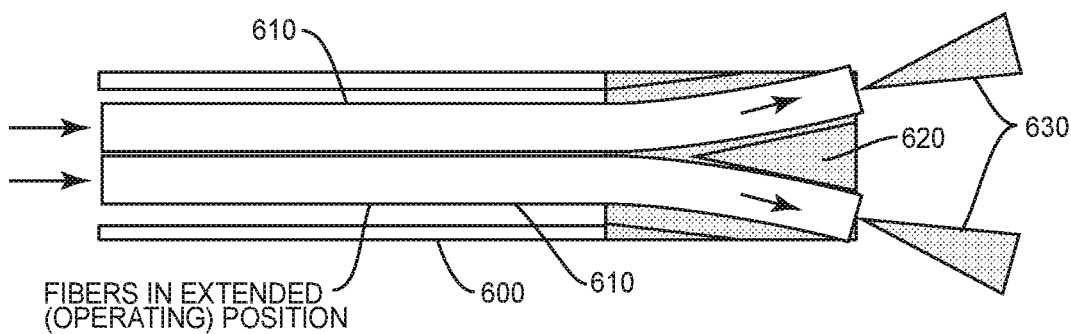

A first example embodiment of the distal end of a multi-fiber multi-spot laser probe that omits a GRIN lens at the distal end is shown in FIGS. 6A and 6B. As seen in the figures, this example laser probe includes fibers 610 with cleaved or polished ends that are movable as a group onto a distal ramp element 620, so that the fibers 610 can be moved between two states. A first state is shown in FIG. 6A, which illustrates a retracted, non-operating position, which provides a compact outer diameter for insertion and extraction, e.g., through small-gauge trocar entry systems. FIG. 6B illustrates an extended, operating position, in which the fibers 610 have been translated towards the distal end of the laser probe and are forced by ramp element 620 to curve outward and at least partially through external openings in the distal end of the laser probe, for delivering angularly separated beams 630 to achieve a multi-spot pattern.

As seen in FIGS. 6A and 6B, ramp element 620 fits into or onto the distal end of cannula 600, which surrounds the fibers 600 along at least the illustrated portion of the laser probe, i.e., at or near the distal end of the laser probe. Ramp element 620 may be formed from a separate machined component having four angled holes converting at its proximal end and diverging distally, which are of sufficient size to allow passage of the fibers. The ramp element may also be manufactured by additive or subtractive microfabrication processes. It will be appreciated that ramp element 620 comprises a channel and/or groove, for each of the fibers 610, such that the fibers 610 are guided by the channels and/or grooves when the fibers 610 are translated towards the distal end, and thus into the extended position, and when the fibers are retracted, towards the proximal end of the probe (not shown), into the retracted position.

Illumination capability can be added to the laser probe illustrated in FIGS. 6A and 6B in any of several ways. Several approaches are based on the use of a nanofiber for carrying visible light to the end of the cannula. It will be appreciated that it is important to minimally obstruct the inner and/or outer diameters of the multi-spot laser probe, and thus the fiber optics diameters should be as small as reasonably possible. Accordingly, several of the embodiments described herein utilize a nanofiber, e.g., made of glass, with a diameter of less than 50 microns for carrying visible light along the cannula, to the distal end of the laser probe.

Notably, the light spreading at the tip of the fiber is another important factor. Described below are three general approaches to achieving a desirable spreading of the visible light as it exits the illumination fiber. These are illustrated in FIGS. 7A, 7B, and 7C.

Figure 7A:
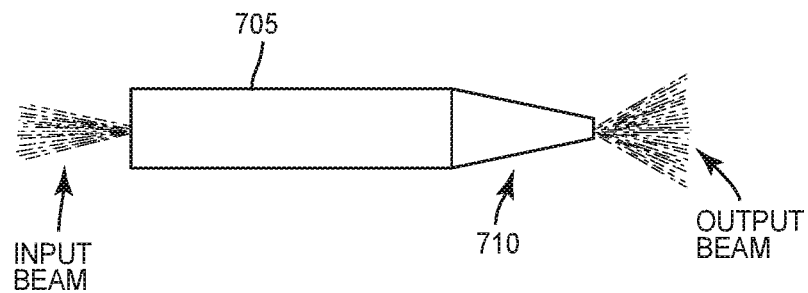
FIG. 7A, FIG. 7B, and FIG. 7C illustrate examples of illumination fiber terminations.

A first approach, as illustrated in FIG. 7A, is to form a tapered tip 710 at the end of the illumination fiber 705. This tapering can be formed by a mechanical process, e.g., polishing, or by a chemical etching process, or by thermal processes. In each case, the result of the tapered tip 710 is that the light emerging from the illumination fiber 705 comes out in a wide angle, where the width of the angle is determined by the angle and length of the taper.

Figure 7B:
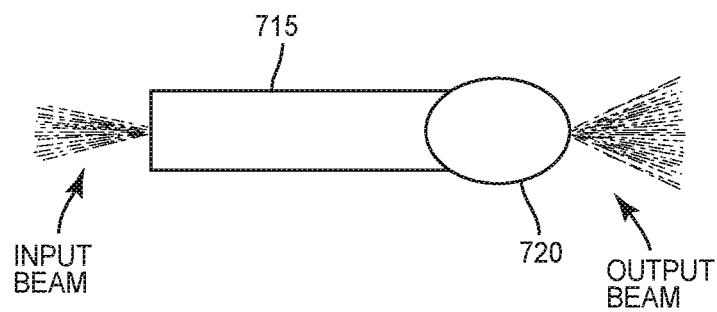

A second approach, illustrated in FIG. 7B, is to form a scattering tip 720, which may be substantially spherical, for example, at the end of the illumination fiber 715. This scattering tip 720 can have a refractive index gradient that causes the light emerging from the end of the illumination fiber 715 to disperse in a desirable scattering pattern. Examples of techniques for forming a scattering tip are described in detail in U.S. Patent Application Publication No. 2017/0176660 A1, published 22 Jun. 2017, the entire contents of which are incorporated herein by reference.

Figure 7C:
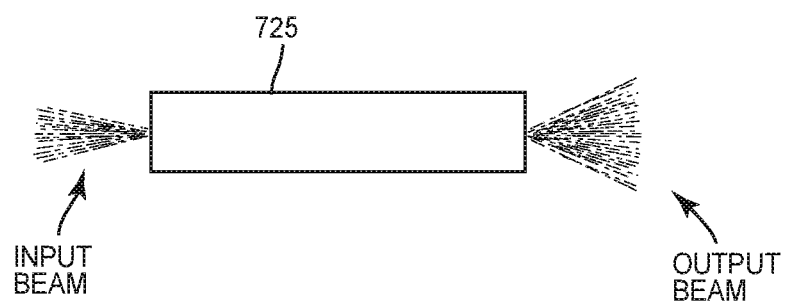

In a third approach, illustrated in FIG. 7C, the illumination fiber 725 is flat cleaved. This requires a high angular launch of the visible light into the fiber 725. The illumination fiber 725 also should have a high numerical aperture to transfer the visible light.

Figure 8A:
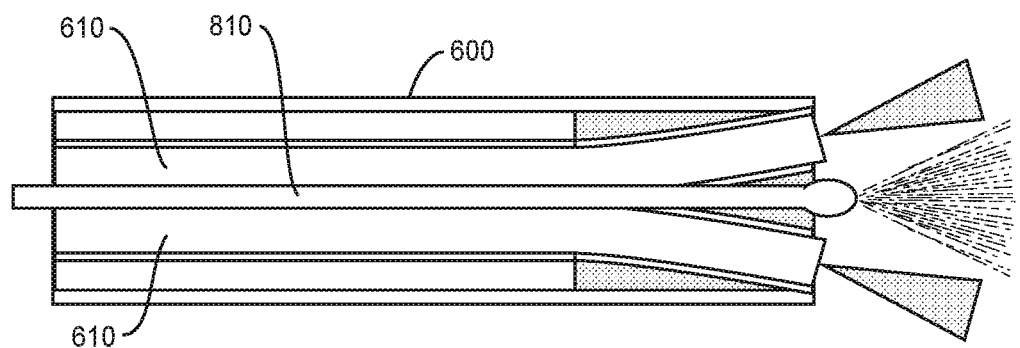
FIG. 8A, FIG. 8B, and FIG. 8C are views of example multi-fiber, multi-spot laser probes that incorporate an illumination fiber.
Figure 8B:
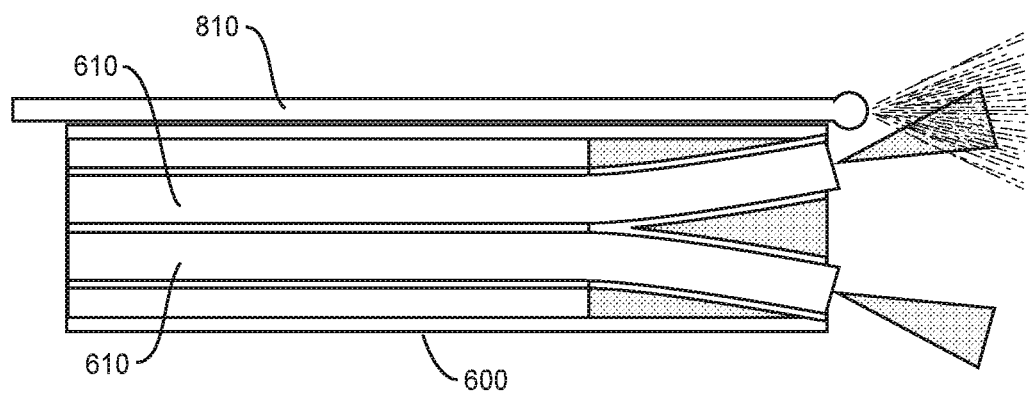

Any one of the approaches shown in FIGS. 7A-7C can be used in combination with the multi-spot laser probe illustrated in FIG. 5 and in FIGS. 6A and 6B. FIGS. 8A and 8B, for example, show two different approaches to adding an illumination fiber to a multi-spot laser probe similar to the one illustrated in FIGS. 6A and 6B. Illustrated in each of these figures is the distal end of a multi-fiber, multi-spot laser probe that comprises multiple fibers 610 (four, in this case) extending from the proximal end of the laser probe to at least near the distal end of the laser probe; as discussed above in connection with FIGS. 1-3, the proximal end of the laser probe is configured to be coupled to a laser source via an adapter interface. As was the case with the laser probe shown in FIGS. 6A and 6B, the laser probes illustrated in FIGS. 8A and 8B each include a cannula 600 having a distal end and surrounding the multiple fibers along at least a portion of the laser probe at or near the distal end of the laser probe.

Figure 8C:
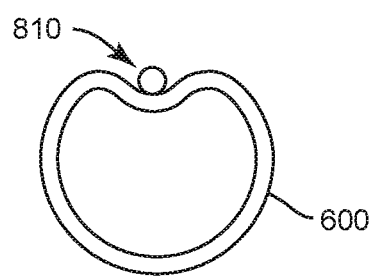
Figure 14:
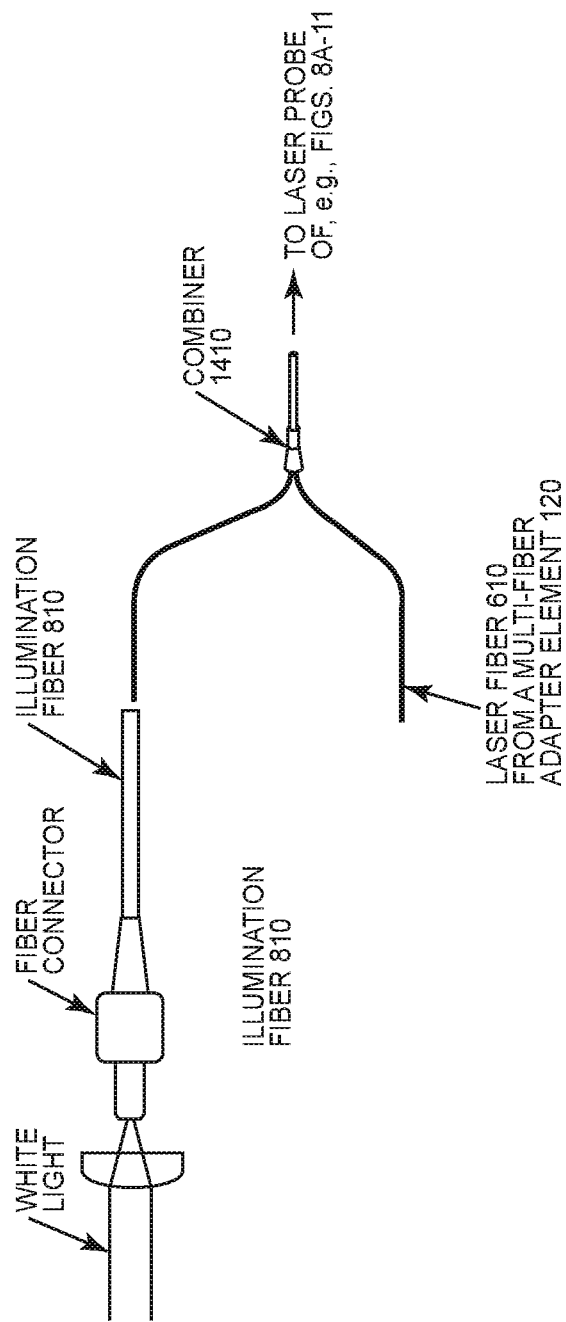
FIG. 14 illustrates an example mechanism for combining an illumination fiber with laser fibers at the proximal end of an example laser probe.
Figure 15:
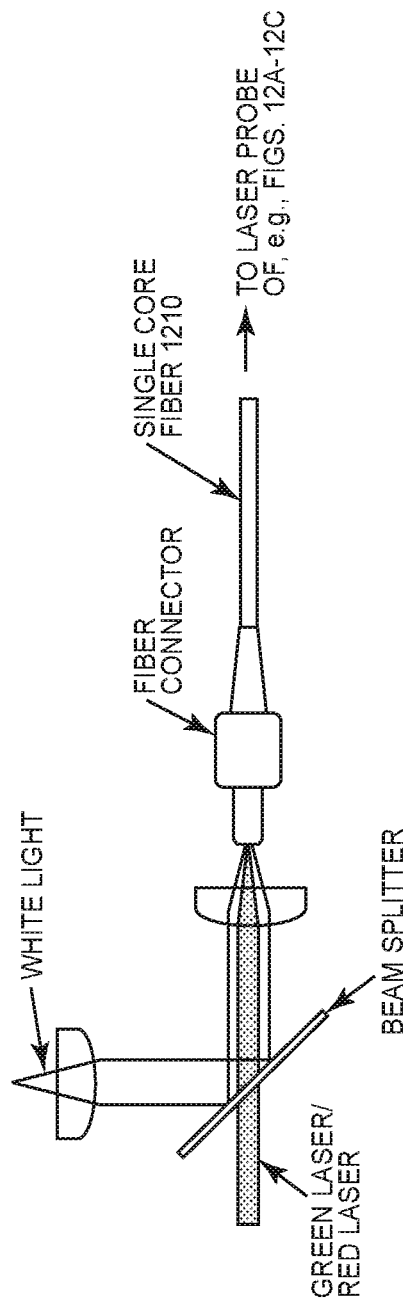
FIG. 15 illustrates an example mechanism for coupling illumination light and laser light into a single core fiber, at the proximal end of an example laser probe.

In each of the examples shown in FIGS. 8A and 8B, the laser probe further includes an illumination fiber 810 extending from the proximal end of the laser probe to at least near the distal end of the laser probe. This illumination fiber 810 has a diameter substantially smaller than corresponding diameters for the fibers, e.g., less than 50 microns, compared to a diameter of 90 microns or more for the fibers 610. Although not shown in FIGS. 8A and 8B, the illumination fiber 810 is arranged, at the proximal end of the fiber, for coupling to a visible light source. FIG. 14 illustrates an example arrangement for coupling the visible light source to the illumination fiber 810. In the illustrated example, illumination fiber 810 and laser fibers 610 are brought together, with combiner 1410, at the proximal end of the laser probe. Note that in FIGS. 8A and 8B, the illumination fiber is shown with a substantially spherical scattering tip, as illustrated in FIG. 7B. It will be appreciated that other approaches for scattering the illumination light as it exits the illumination fiber 810, including those approaches shown in FIGS. 8A and 8C, may be used instead.

In the example shown in FIG. 8A, the illumination fiber 810 extends along the laser probe within the cannula 600. In this case, the illumination fiber 810 is arranged at approximately the longitudinal center of the cannula 600. In other embodiments, the illumination fiber 810 might not be centered—for example, the illumination fiber 810 may be arranged along the inside wall of the cannula 600, in some embodiments.

In contrast to the example of FIG. 8A, in the example shown in FIG. 8B, the illumination fiber 810 instead extends along the laser probe outside the cannula 600, along an exterior surface of the cannula 600. In some embodiments, the illumination fiber 810 may be arranged in a groove 815 that extends longitudinally along at least a portion of the cannula 600. A simplified cross-section illustrating the arrangement of illumination fiber 810 in the groove 815 is provided in FIG. 8C; it will be appreciated that the fibers 610 and other components inside the cannula 600 are omitted from this figure, for simplicity.

Figure 9A:
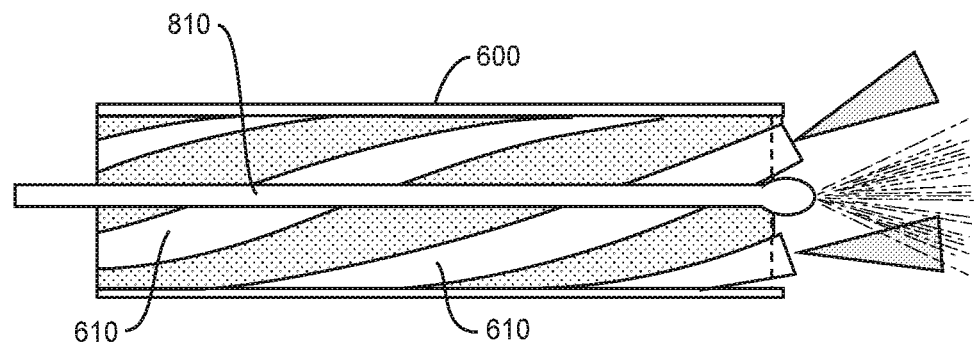
FIG. 9A and FIG. 9B are views of other example multi-fiber, multi-spot laser probes that incorporate an illumination fiber.
Figure 9B:
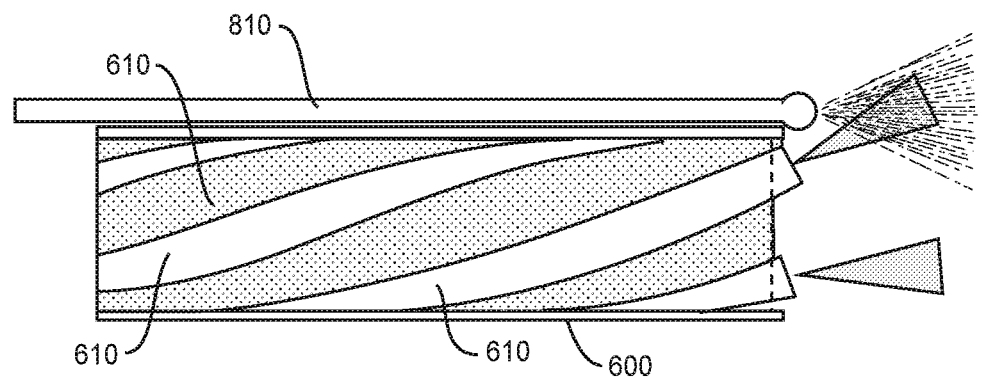

FIGS. 9A and 9B illustrate two additional examples of a multi-fiber, multi-spot laser probe that includes an illumination fiber 810. Again, each of these figures illustrates the distal end of a multi-fiber, multi-spot laser probe that comprises multiple fibers 610 (four, in this case) extending from the proximal end of the laser probe to at least near the distal end of the laser probe. Again, the laser probes each include a cannula 600 having a distal end and surrounding the multiple fibers along at least a portion of the laser probe at or near the distal end of the laser probe. In these embodiments, the laser probes each include a helical spacer 915, arranged within cannula 600, where the helical spacer 915 creates tangential angular separation of the fibers 610, by arranging them in a helical configuration.

It will be appreciated that this configuration allows for a continuous central area between the fibers 610, providing a convenient location for disposing an illumination fiber 810 that extends along the laser probe within the cannula 600, as shown in FIG. 9A. Once again, this illumination fiber 810 has a diameter substantially smaller than corresponding diameters for the fibers, e.g., less than 50 microns, compared to a diameter of 90 microns or more for the fibers 610. Again, the illumination fiber 810 is shown with a substantially spherical scattering tip, as illustrated in FIG. 7B, but it will be appreciated that other approaches for scattering the illumination light as it exits the illumination fiber 810 may be used instead. One or more other fibers might also occupy this central passage in the cannula 600, in some embodiments.

Alternatively, as shown in FIG. 9B, the illumination fiber 810 extends along the laser probe outside the cannula 600, along an exterior surface of the cannula 600. In some embodiments, the illumination fiber 810 may be arranged in a groove that extends longitudinally along at least a portion of the cannula 600, as was shown in FIG. 8C.

Figure 10A:
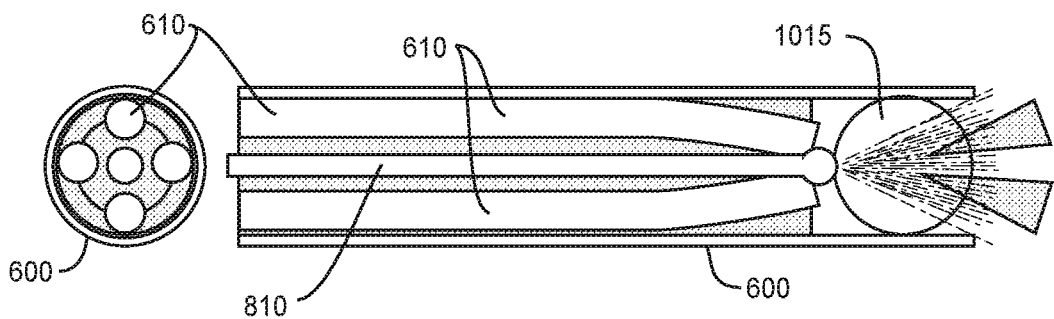
FIG. 10A, FIG. 10B, and FIG. 10C are views of example multi-fiber, multi-spot laser probes that incorporate an illumination fiber as well as lens elements disposed at the distal end of the laser probe cannula.
Figure 10B:
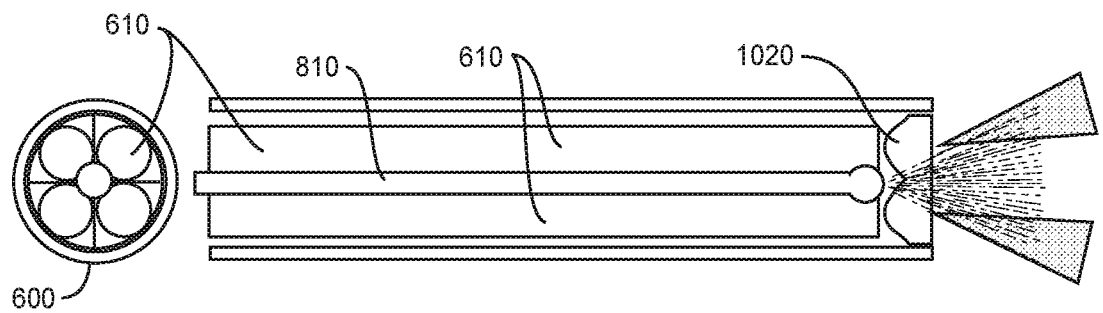
Figure 10C:
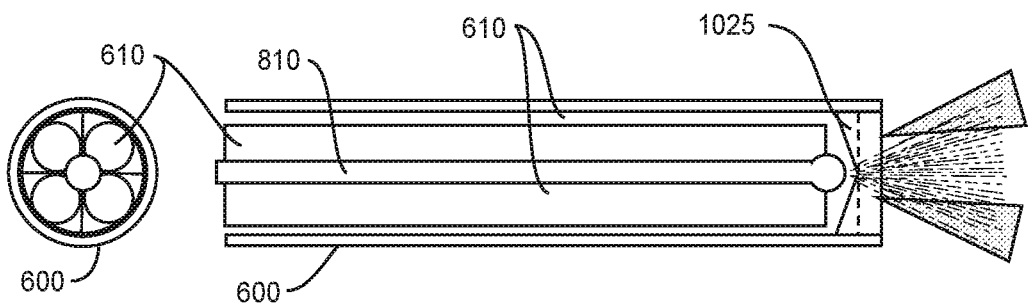

Illumination fibers 810 like those shown in the examples of FIGS. 7A-7C, 8A-8C, 9A, and 9B may also be employed in multi-fiber, multi-spot laser probes that further include a lens element inside the cannula 600, at or near the distal end of the cannula 600. Examples of these embodiments are illustrated in FIGS. 10A, 10B, and 10C, with these examples featuring a ball lens 1015, a micro-lens array 1020, and a micro-wedge array 1025, respectively. With the micro-lens array 1020 and micro-wedge array 1025, each element of the array is paired with a corresponding fiber. More generally, these lens elements are each arranged such that light from the illumination fiber 810 passes through the lens element, along with light from the fibers 610. It will be appreciated that these lens elements may be configured, in various embodiments, to provide beams with near-field focus, collimation, or mildly diverging properties. These can provide several advantages, depending on the degree of beam focusing, including that stronger beam focusing can provide near-field convergence of the individual beams that can substantially overlap, providing essentially a single beam at a working distance approximately equal to the focal length, while providing individual beams at longer working distances. Alternatively, lenses adapted to provide collimation or near-collimation can provide a design that is insensitive to working distance and therefore provides greater ease of use, with smaller spots, and thus requires less total power to provide the required intensity for surgical treatment. Lenses configured to provide slight beam divergence can be used to provide embodiments that produce adequate spot separation at shorter working distances, while still providing relatively low sensitivity to working distance, compared to the raw output from non-lensed fibers.

Figure 11:
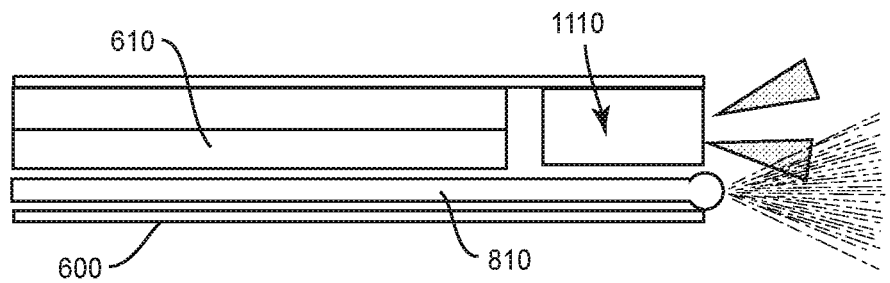
FIG. 11 illustrates another example laser probe that includes a GRIN lens disposed at the distal end of the laser probe cannula.

FIG. 11 illustrates still another example of a deployment of an illumination fiber 810 in a multi-spot laser probe. In this example, the illumination fiber 810 is deployed within the cannula 600, along an inner wall of the cannula 600. The laser-delivery fibers 610 in this example stop short of the distal end of the cannula 600, and a lens element 1110, in this case a GRIN lens, is positioned within the cannula 600, at or near its distal end. Note that in this embodiment, the lens element 1110 is arranged such that light from the fibers 610 passes through the lens element 1110, but light from the illumination fiber 810 does not.

Figure 12A:
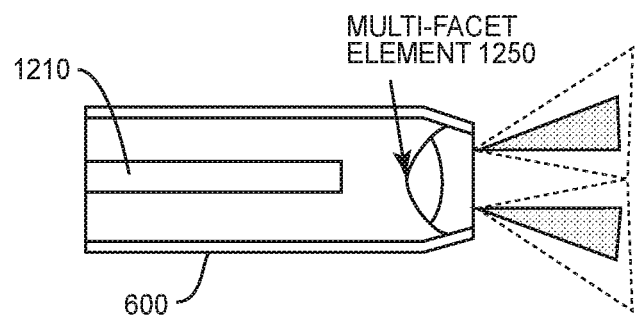
FIG. 12A, FIG. 12B, and FIG. 12C illustrate examples of laser probe configurations in which illumination fiber is carried in a fiber that also carries laser light.
Figure 12B:
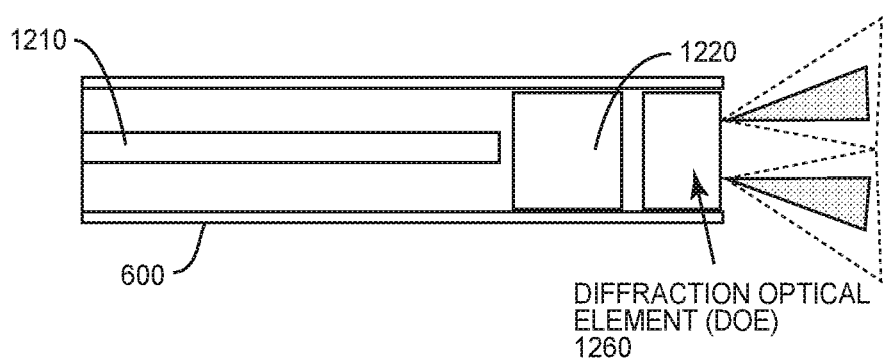
Figure 12C:
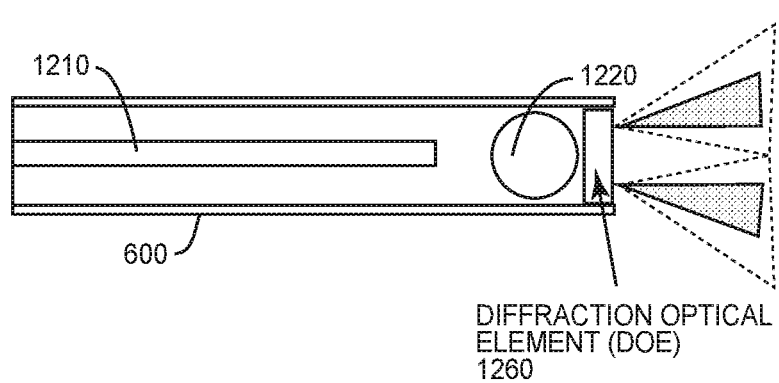

The example embodiments described above include embodiments in which visible light is delivered to the distal end of the laser probe via a separate fiber. Another approach is to use a fiber that is used to deliver laser light for delivery of the visible light as well. Several examples of this approach are illustrated in FIGS. 12A, 12B, 12C. The example shown in FIG. 12A utilizes a multi-facet optical element to split the single beam from the distal fiber tip into multiple (four in this figure) beams. The examples shown in FIGS. 12B and 12C utilize a GRIN lens 1220, and a sapphire lens 1230, respectively, arranged inside the cannula 600 at its distal end, such that both laser light and visible light from fiber 1210 passes through the lens. The light is split by the diffraction optical element (DOE) 1260 in front of the GRIN lens 1220 or sapphire lens 1230.

Figure 13:
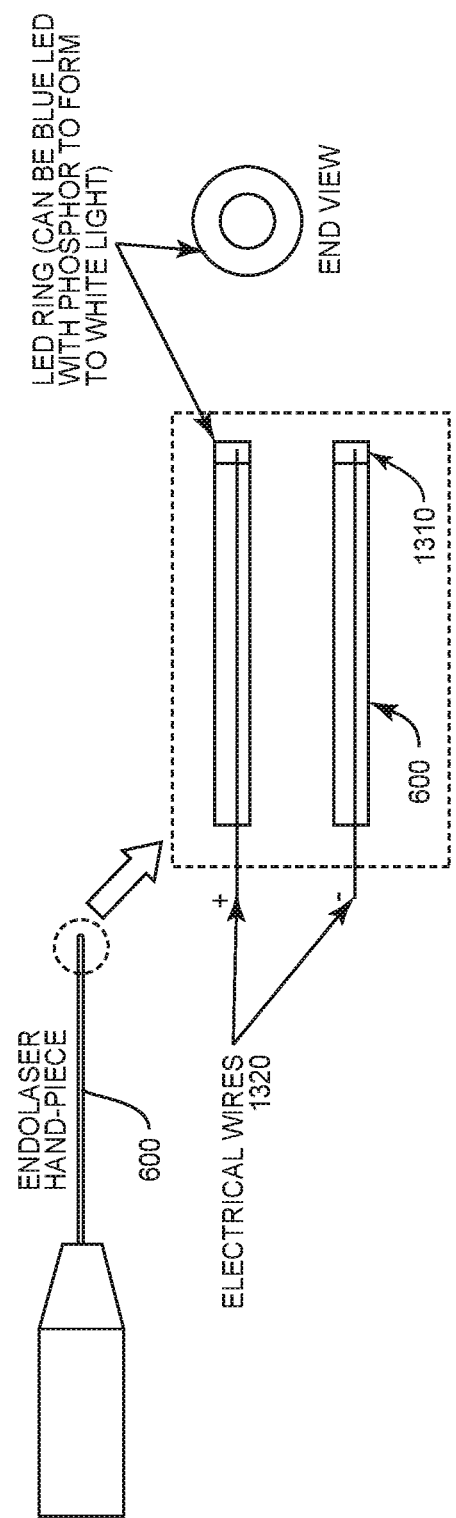
FIG. 13 illustrates an example laser probe that includes an LED ring at the distal end of the laser probe cannula.

FIG. 13 illustrates still another example approach for delivering illumination from the distal end of a laser probe. In this example, the laser probe comprises one or more fibers that extend from a proximal end of the laser probe to at least near a distal end of the laser probe. The laser probe further includes a cannula 600 having a distal end and surrounding the one or more fibers along at least a portion of the laser probe at or near the distal end of the laser probe. In FIG. 13, these one or more fibers are omitted from the drawing, for simplicity. The example laser probe of FIG. 13 further includes a light-emitting diode attached to the cannula at or near the distal end of the cannula 600, the light-emitting diode being electrically coupled, with electrical wires 1320, to a power source via the adapter interface of the laser probe.

In some embodiments, e.g., as shown in FIG. 13, the light-emitting diode forms part of a light-emitting diode ring 1310 that encircles the cannula 600 at or near the distal end of the cannula 600. In some embodiments, the light-emitting diode ring 1310 comprises a light guide for directing light from the light-emitting diode towards an illuminated region beyond the distal end of the laser probe. The light-emitting diode ring 1310 may include a blue LED with phosphor, to form white light.

Various embodiments described above and illustrated in the attached figures provide for the addition of illumination to a laser probe, with minimal impacts on the size and shape of the laser probes. This is particularly important in the context of multi-fiber, multi-spot, laser probes, where the constraints on the outer diameter of the laser probe cannula are already tight. Several of the described approaches allow for the addition of illumination to such probes without any need to increase the cannula gauge size. The use of glass nanofibers to carry the visible light to the distal end of the cannula, in some embodiments, provides additional advantages, compared to plastic optical fiber, in that this approach provides improved thermal robustness.

The various embodiments described herein address several needs for multi-spot laser probes, with the added illumination. Embodiments may enable self-scleral depression for peripheral visualization/access. They may enable bimanual surgery, without the fourth chandelier incision. Further, they may provide additional task lighting.

Embodiments described above illustrate but do not limit the invention. It should also be understood that numerous modifications and variations are possible in accordance with the principles of the present invention.

What is claimed is:

1. A multi-fiber, multi-spot laser probe, comprising:
a plurality of fibers extending from a proximal end of the laser probe to at least near a distal end of the laser probe, wherein the proximal end of the laser probe is configured to be coupled to a laser source;
a cannula having a distal end and surrounding the plurality of fibers along at least a portion of the laser probe at or near the distal end of the laser probe; and
an illumination fiber extending from the proximal end of the laser probe to at least near the distal end of the laser probe, wherein the illumination fiber has a diameter substantially smaller than corresponding diameters for the plurality of fibers and is arranged, at the proximal end of the illumination fiber, for coupling to a visible light source;
wherein the illumination fiber extends along the laser probe within the cannula;
wherein the illumination fiber is arranged at approximately a longitudinal center of the cannula;
wherein the plurality of fibers are movable as a group onto one or more distal ramps that are configured to curve the plurality of fibers outward relative to each other;
wherein the illumination fiber is fixed relative to the probe such that the plurality of fibers move relative to the fixed illumination fiber.

2. The multi-fiber, multi-spot laser probe of claim 1, wherein each of the plurality of fibers has a diameter of at least 90 microns, and wherein the illumination fiber has a diameter of less than 50 microns.

3. The multi-fiber, multi-spot laser probe of claim 1, wherein the illumination fiber extends to near the distal end of the cannula, but short of the distal end of the cannula, and wherein the multi-fiber, multi-spot laser probe further comprises a lens element inside the cannula, at or near the distal end of the cannula, such that light from the illumination fiber passes through the lens element.

4. The multi-fiber, multi-spot laser probe of claim 3, wherein the lens element is one of:
a ball lens;
a micro-lens array; and
a micro-wedge array.

5. The multi-fiber, multi-spot laser probe of claim 1, wherein the multi-fiber, multi-spot laser probe further comprises a lens element inside the cannula, at or near the distal end of the cannula, but arranged such that light from the plurality of fibers passes through the lens element but light from the illumination fiber does not pass through the lens element.

6. A laser probe, comprising:
a plurality of fibers extending from a proximal end of the laser probe to at least near a distal end of the laser probe, wherein the proximal end of the laser probe is configured to be coupled to a laser source;
a cannula having a distal end and surrounding the one or more plurality of fibers along at least a portion of the laser probe at or near the distal end of the laser probe;
a light-emitting diode attached to the cannula at or near the distal end of the cannula, the light-emitting diode being electrically coupled to a power source; and
an illumination fiber extending from the proximal end of the laser probe to at least near the distal end of the laser probe, wherein the illumination fiber has a diameter substantially smaller than corresponding diameters for the plurality of fibers and is arranged, at the proximal end of the illumination fiber, for coupling to the light emitting diode:
wherein the illumination fiber extends along the laser probe within the cannula;
wherein the illumination fiber is arranged at approximately a longitudinal center of the cannula;
wherein the plurality of fibers are movable as a group onto one or more distal ramps that are configured to curve the plurality of fibers outward relative to each other;
wherein the illumination fiber is fixed relative to the probe such that the plurality of fibers move relative to the fixed illumination fiber.

7. The laser probe of claim 6, wherein the light-emitting diode forms part of a light-emitting diode ring that encircles the cannula at or near the distal end of the cannula.

8. The laser probe of claim 7, wherein the light-emitting diode ring comprises a light guide for directing light from the light-emitting diode towards an illuminated region beyond the distal end of the laser probe.

* * * * *